United States Patent [19]

Evans

[11] Patent Number: 5,007,917
[45] Date of Patent: Apr. 16, 1991

[54] SINGLE BLADE CUTTER FOR ARTHROSCOPIC SURGERY

[75] Inventor: James A. Evans, Galesburg, Mich.

[73] Assignee: Stryker Corporation, Kalamazoo, Mich.

[21] Appl. No.: 490,913

[22] Filed: Mar. 8, 1990

[51] Int. Cl.⁵ .............................................. A61B 17/00
[52] U.S. Cl. ...................... 606/170; 606/79; 606/167; 606/180; 604/22
[58] Field of Search ............... 606/159, 167, 170, 180, 606/179, 79; 604/22

[56] References Cited

U.S. PATENT DOCUMENTS

| | | |
|---|---|---|
| 3,618,611 | 11/1971 | Urban . |
| 3,732,858 | 5/1973 | Banko . |
| 3,945,375 | 3/1976 | Banko . |
| 4,203,444 | 5/1980 | Bonnell et al. . |
| 4,274,414 | 6/1981 | Johnson et al. . |
| 4,368,734 | 1/1983 | Banko . |
| 4,512,344 | 4/1985 | Barber . |
| 4,517,977 | 5/1985 | Frost . |
| 4,649,919 | 3/1987 | Thimsen et al. . |
| 4,834,729 | 5/1989 | Sjostrom .............................. 606/170 |
| 4,850,354 | 7/1989 | McGurk-Burleson .............. 606/170 |
| 4,867,157 | 9/1989 | McGurk-Burleson et al. .... 606/170 |

Primary Examiner—Mickey Yu
Assistant Examiner—Kerry Owens
Attorney, Agent, or Firm—McAndrews, Held & Malloy

[57] ABSTRACT

A surgical instrument having a tube and a rotating cutter head. The cutter head has a sole blade bearing two cutting edges extending from a cylindrical base and meeting in a point. An helical debris channel follows from the blade point through the cylindrical base so that large pieces of tissue may be cut and carried away by suction within the tube.

8 Claims, 1 Drawing Sheet

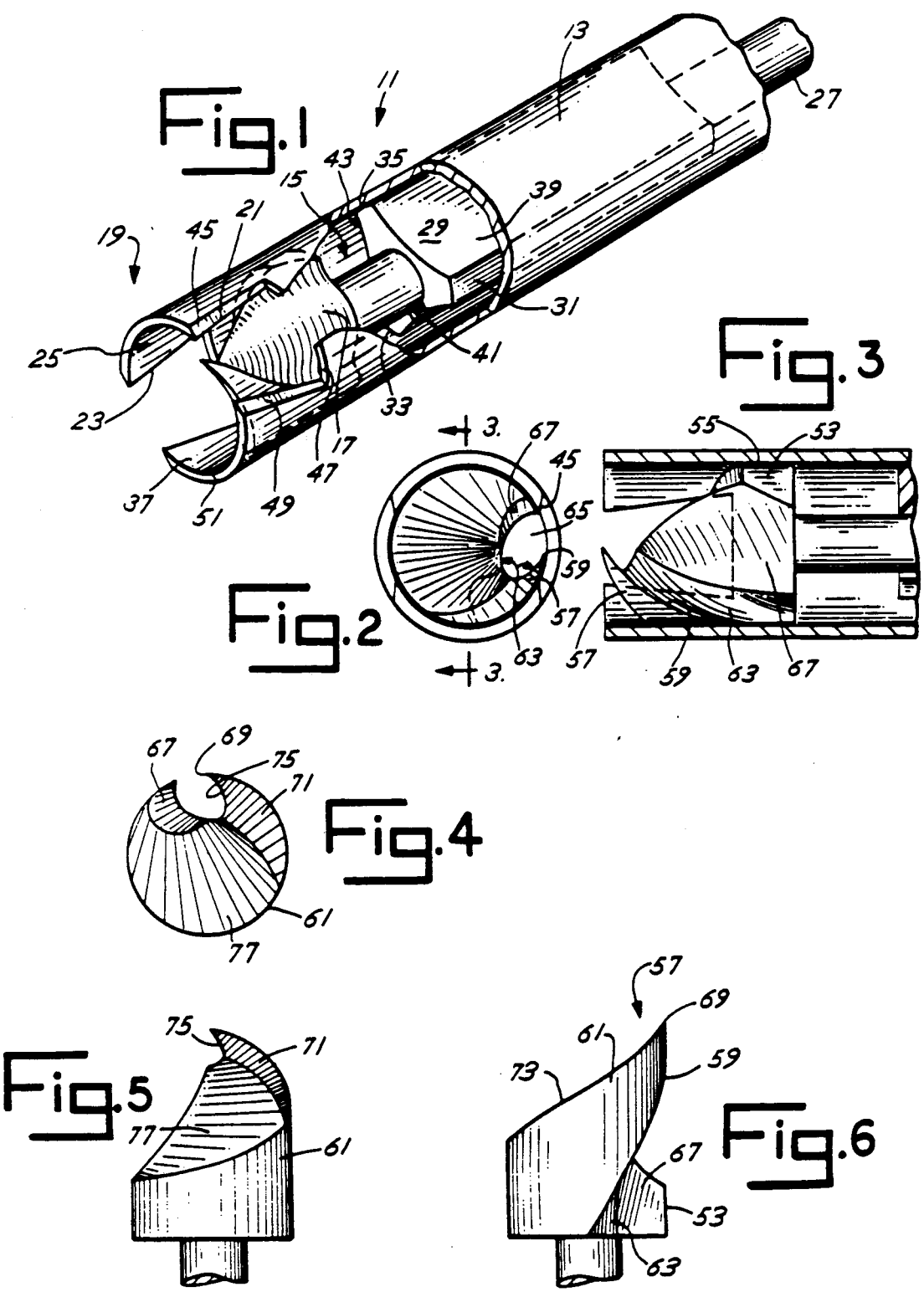

SINGLE BLADE CUTTER FOR ARTHROSCOPIC SURGERY

BACKGROUND OF THE INVENTION

The invention relates to a surgical cutting instrument having a rotating cutter within a stationary outer tube. The outer tube has an open end adjacent to the cutter and one or more side openings having edges that cooperate with the rotating cutter to cut tissue. This type of cutter, when sized and constructed for insertion into a joint, is particularly useful for arthroscopic surgical procedures.

Surgical cutters constructed with an outer guide tube and an inner cutting member are known in the art. The tube and cutter are generally sized and constructed for specific surgical uses. Significant factors influencing the viability of a cutter include the type of tissue to be cut and the rate at which tissue is to be cut. The mechanism for cutting the specific tissue at the desired rate and consequently the design of the cutting structure embody the most significant differences among these cutters.

U.S. Pat. Nos. 3,618,611, 4,203,444, 4, 274,414, and 4,368,734 are representative of surgical cutters that are constructed with a stationary outer tube and a rotating inner tube. U.S. Pat. No. 3,618,611 discloses a cutter for delicate surgical removal of tissue which has tubes with adjacent openings in the sides of bullet shaped ends. The inner tube has multiple cutting points in the edge of the opening in the inner tube. As the inner tube is rotated, tissue is captured when the openings are aligned and sheared as the inner tube is rotated. U.S. Pat. Nos. 4,203,444 and 4,274,414 disclose concentric tube cutters constructed for arthroscopic surgery of joints. U.S. Pat. No. 4,368,734 discloses a cutter constructed for removal of relatively hard tissue of advanced cataracts.

U.S. Pat. Nos. 3,732,858, 3,945,375, 4,512,344, 4, 517,977, and 4,649,919 are representative of surgical cutters that are constructed with an outer tube and a solid cutter rotating within the outer tube. U.S. Pat. No. 3,732,858 and 3,945,375 disclose surgical cutters for removal of tissue from the eye. The cutters disclosed by these patents have an outer tube with a closed or partially open end and drill-like solid cutters. U.S. Pat. No. 4,512,344 discloses a surgical cutter for arthroscopic surgery having an outer tube with an open end and one or more side openings. The inner cutters have generally longitudinal cutting edges lying along the axis of the cutter and a cutting edge lying in an axial plane. U.S. Pat. No. 4,517,977 discloses a surgical cutter for removal of fibrous brain tissue. The outer tube has closed sides and a partially open end. The solid cutter has a cutting edge lying in a radial plane. U.S. Pat. No. 4,649,919 discloses a surgical cutter for arthroscopic joint surgery having an outer tube with an open end and two side openings extending from the end of the tube. The inner cutter is recessed from the end of the tube and has an auger-like cutter having a "fish-tailed" end profile. A cutting edge extends radially along each blade of the cutter providing two concave cutting edges. The radial extent of each blade may be provided with a short cutting edge. The outer tube has tabs that extend beyond the inner cutter and over a small portion of the radial extent of the inner cutter.

Surgical cutters known in the art may have general application, but are best suited to a particular surgical use. Tissue characteristics, the amount of tissue and rate of removal vary significantly among surgical uses. Aggressive cutting and removal of a significant amount of tough tissue, such as fibrous cartilage of the knee presents a difficult surgical use for which some cutters known in the art ar not ideally suited.

SUMMARY OF THE INVENTION

In accordance with the present invention, an end cutter for aggressive cutting of tough tissue of a human joint by arthroscopic surgery overcomes shortcomings of cutters known in the art. The cutter of the present invention is more durable and capable of cutting and removing larger pieces of tissue than cutters of the prior art.

More particularly, the surgical cutter embodiment of the present invention includes a stationary outer tube having an open end and side windows extending from the end. A solid rotating single blade tissue cutter is positioned within the outer tube at the tube end. A sole leading, tissue penetrating blade is formed in the tissue cutter and is positioned to one circumferential side of the cutter leaving a large area for a helical debris channel. The end surface of the cutter is formed to spiral from a tissue penetrating point of the blade to a level below the maximum extent of the side window. The intersection of the debris channel and the end surface adjacent to the tissue penetrating point forms an end cutting edge which cuts tissue entering the end of the stationary tube. The intersection of the debris channel and the outer surface of the tissue cutter forms as a side cutting edge which cooperates with an edge of the side window to cut tissue that enters through the side window.

The profile of the tissue penetrating point and the cutting edges are determined by the helical angle of the debris channel, the cross sectional shape of the debris channel, and the spiral profile of the end surface. Because a single cutting blade and a single debris channel are formed by the cutter, a wider range of profiles may be formed by a cutter according to the present invention than cutters having multiple cutting structures.

It is therefore an object of the present invention to provide a surgical cutter that can aggressively cut tough tissue.

Another object of the present invention is to provide a surgical cutter with a large debris channel so that pieces of tissue that are large relative to the size of the cutter may be cut and transported through the cutter.

A further object of the present invention is to provide a surgical cutter that can cut large pieces of tissue at the end of the cutter and the side of the cutter.

These and other objects, advantages and novel features of the present invention, as well as details of an illustrative embodiment thereof, will be more fully understood from the following description and from the drawings.

BRIEF DESCRIPTION OF THE DRAWINGS

FIG. 1 is a partial cutaway perspective view of the surgical single blade cutting instrument of the present invention.

FIG. 2 is an axial end view of the surgical instrument of FIG. 1.

FIG. 3 is a side view of the cutter head and a section view of the outer tube taken along line 3—3 of FIG. 2.

FIG. 4 is an end view of the tissue cutter head.

FIG. 5 is a side view of the tissue cutter head.

FIG. 6 is a side view of the tissue cutter head shown 90° with respect to the side view of FIG. 5.

DETAILED DESCRIPTION OF THE PREFERRED EMBODIMENT

Referring to FIG. 1, a surgical instrument 11 is formed from a cylindrical tube 13 and a cutter assembly 15. Assembly 15 includes a cutter head 17 which rotates relative to the distal end 19 of tube 13 and relative to a pair of windows 21, 23 formed in the distal end 19. Tissue enters the end opening 25 of the tube or enters through windows 21, 23 for cutting.

Cutter head 17 is held in an axially fixed position relative to tube 13 and is rotated counterclockwise as viewed from the distal tube end 19. A cylindrical shaft 27 is secured between cutter head 17 and a conventional surgical instrument motor (not shown) for rotating the shaft. The cutter may be rotated at any velocity. The velocity for most effective cutting depends upon the characteristics of the tissue and other factors. Velocities of 1800 rpm to 3200 rpm have been found to produce effective cutting. A plastic shaft support 29 is frictionally fit around shaft 27 in relative close proximity to cutter head 17 for providing a rotational bearing to the cutter head. The shaft support 29 is located generally adjacent to cutter head 17 to maintain alignment of shaft 27 and cutter head 17 within tube 13. A shoulder or key (not shown) may be used to locate support 29 along the shaft.

Shaft support 29 is generally triangular in cross-section having three edge surfaces 31, 33, 35 which bear against the inside wall 37 of tube 13. Between edge surfaces 31, 33, 35, three inwardly curved surfaces 39, 41, 43 form the remaining exterior peripheria of support 29. Debris passages are formed by each curved surface 39-43 and the inside wall 37 of the tube. A conventional vacuum suction device (not shown) is secured to an opening in the proximal end of the tube for sucking cut tissue debris from the cutter head area and through the three passages formed around spacer element 29.

Each of windows 21, 23 are formed by a single cutting edge 45, a proximal edge 47 and a leading edge 49. Window 21 in tube 13 is formed to define an acute angle with inner surface 37 at cutting edge 45. Leading edge 49 is met first by the cutter head during its counterclockwise rotation and cutting edge 45 follows. The distal edge of windows 21, 23 is removed, defined by the circular locus of the plane of the distal edge 51 of the tube. The plane of the distal edge is orthogonal to the axis of tube 13.

As shown in FIG. 3, cutter head 17 includes a cylindrical base portion 53 having an outer cylindrical surface 55 which bears against the inside surface 37 of the tube. Cylindrical surface 55 circumscribes more than 180° of the inside surface of the tube, leaving some of its extent for passage of debris, as described hereinafter. Cylindrical base portion 53 is disposed below windows 21, 23, as seen in FIG. 3, and forms the base of the cutter head.

As shown in FIG. 6, base portion 53 carries a sole flute or blade 57 which is positioned to one circumferential side of the cutter head, as best seen in FIG. 2. Blade 57 has a cutting edge 59 which traces a generally helical path from top to bottom, as seen in FIG. 6. Cutting edge 59 provides a point intersection with the straight cutting edge 45 of each window 21, 23 as the blade rotates in a counterclockwise direction. This point intersection of the helical edge 59 and the straight edge 45 provides a scissor-like action to shear tissue protruding into tube 13 through windows 21, 23.

Helical cutting edge 59 is formed in the outer cylindrical surface 61 of the cutter head, which is an extension of the outer cylindrical surface 55 of base portion 53. Cutting edge 59 is formed from the intersection of cylindrical surface 61 and a grooved surface 63 (FIG. 3).

Grooved surface 63 forms one side of a helical debris channel 65 (FIG. 2), through which cut tissue is sucked to the proximal end of the tube. As seen in FIG. 2, grooved surface 63 is disposed at an acute curved angle with respect to outer cylindrical surface 61 for providing a sharp cutting edge 59. As cutting edge 59 meets with the cutting edge 45 of the window, the cut tissue moves into channel 65 of the cutter head.

As seen in FIGS. 2 and 3, the other side of channel 65 is formed by a second curved surface 67. As understood, debris channel 65 passes under blade 57 as viewed in FIG. 2 and shown by the dashed line.

Referring to FIG. 4, blade 57 is brought to a point 69 by a generally flat end surface 71 which tapers downwardly as defined by top edge 73 (FIG. 6). As shown in FIGS. 4 and 5, a cutting edge 75 is formed in the top of blade 57 by the intersection of generally flat surface 71 with grooved surface 63. A second end surface 77 continues the taper of flat surface 71, leading downwardly to debris channel 65.

As best shown in FIGS. 1 and 2, tissue may be drawn into distal end 19 of tube 13. As shown in FIGS. 1 and 3, rotation of cutter head 17 to advance helical edge 59 towards cutting edge 45 will cause tissue in distal end 19 to enter debris channel 65 and counter clockwise rotation will cause cutting edge 75 to function as an impact cutter to cut tissue extending into debris channel 65.

What is claimed is:

1. A surgical instrument for cutting tissue comprising:
    a cylindrical tube having an open distal end and a side window formed in its distal end through which tissue may enter said tube for cutting;
    a tissue cutter head rotatable within said tube relative to said open end and said window, said cutter head including:
    (i) a cylindrical base portion having a radial surface closely conforming to the inside surface of said tube;
    (ii) a sole blade located along one circumferential side of and extending distally from said base portion and bearing a first and a second cutting edge, said first cutting edge disposed on said blade for traveling in a cylindrical locus closely adjacent to the inside surface of said tube relative to said window for passing across one edge of said window during at least a portion of the rotation of said cutter head for cutting tissue protruding laterally through said window, and said second cutting edge for cutting tissue protruding axially through said distal end, said first and second cutting edges meeting in a sole point, said sole point being the most distal point of said cutter head, and
    (iii) a sole debris channel formed by a cavity in said cutter head and passing through said base portion for receiving tissue severed by said first and second cutting edges.

2. A surgical instrument for cutting tissue comprising:
    a cylindrical tube having a central axis, an open end defined by a distal tube edge generally lying in a plane perpendicular to the tube axis, and a side window extending generally axially from the distal tube edge;

said side window being defined by first and second generally straight window side edges extending from corners formed with said distal tube edge and terminating at a proximal boundary of said side window;

a tissue cutter head rotatable within the tube and positioned within the tube generally adjacent to the side window having:

a radial surface closely conforming to the tube;

a debris channel defining a generally helical path along the radial surface and extending proximally beyond the proximal boundary of said side window of the tube and opening within the tube;

said debris channel defining a proximal channel edge and a distal channel edge in the radial surface;

a generally spiral distal surface bounded by an intersection with the debris channel to form a distal debris channel boundary and an intersection with the radial surface that forms a helical distal radial surface boundary from a farthest distal extent adjacent to the distal tube edge at an intersection with the distal channel edge to a proximal extent at an intersection of the proximal channel edge at a location lying in the plane of the proximal side window boundary;

the debris channel and the distal surface having converging helical profiles to intersect at the farthest distal extent of the cutter at the radial surface to form a piercing point at the intersection of the distal radial surface boundary and the proximal channel edge;

the distal surface and debris channel intersecting at the distal debris channel boundary to form a distal cutting edge; whereby, rotation of the single blade cutter within the tube causes the cutting point to approach a corner defined by the distal tube edge and a side edge, further rotation of the single flute cutter causes the cutting point to rotate past the corner and the distal channel edge to continuously pass the side edge and a location of the passing of the distal channel edge and side edge becomes farther proximal from the distal tube edge with rotation of the single blade cutter causing a shearing action between the distal channel edge and the side edge and rotation of the cutter rotates the distal cutting edge and cutting of tissue entering the open distal end of the tube.

3. The surgical instrument of claim 2 having a second window in the side of the tube at a location separated from the side window defined by first and second generally straight window side edges extending from the distal tube edge and terminating at a second side window proximal boundary lying in the plane of the side window proximal boundary, whereby the cutting action of the single flute cutter with the side window during rotation of the single flute cutter will be duplicated with the second side window.

4. The surgical instrument of claim 3 wherein the boundaries of the side windows form a cutting edge at an intersection with an interior surface of the tube.

5. The surgical instrument of claim 4 wherein the single flute cutter head has a proximal boundary surface lying in a plane generally perpendicular to the tube axis at a location proximal to the side window proximal boundary, the debris channel opens to the interior of the tube at the proximal boundary surface and a drive shaft having a cross section much smaller than the cutter and lying along the tube axis is rigidly attached to the single flute cutter, whereby the single flute cutter may be rotated by the drive shaft and a large channel defined by the interior of the tube and the drive shaft provides a path for removal of cut tissue.

6. The surgical instrument for cutting tissue of claim 5 further comprising a drive shaft support attached to the drive shaft proximal to the single flute cutter having a central portion attached to the shaft and extending axially along the shaft and a plurality of centering members extending to the interior of the tube and separated from each other forming channels bounded by the interior of the tube, centering members, and central section that provide a path for removal of cut tissue, whereby deflection of the drive shaft is restrained providing support for the single flute cutter.

7. The surgical instrument for cutting tissue of claim 6 wherein the outer diameter of the tube is approximately 5.0 millimeters.

8. The surgical cutter for cutting tissue of claim 6 wherein the outer diameter of the tube is approximately 4.0 millimeters.

* * * * *